United States Patent [19]  [11]  4,341,706
Christensen et al.  [45]  Jul. 27, 1982

[54] PROCESS FOR THE PREPARATION OF CARBAPENEM ANTIBIOTICS

[75] Inventors: Burton G. Christensen, Scotch Plains; David H. Shih, Manalapan, both of N.J.

[73] Assignee: Merck & Co., Inc., Rahway, N.J.

[21] Appl. No.: 196,005

[22] Filed: Oct. 10, 1980

[51] Int. Cl.³ .............................................. C07D 487/04
[52] U.S. Cl. ...................... 260/245.2 T; 260/239 A; 546/272
[58] Field of Search .................. 260/245.2 T; 546/272

[56] References Cited

U.S. PATENT DOCUMENTS 4,223,038 9/1980 Smale .......................... 260/245.2 T
4,262,009 4/1981 Christensen et al. ........ 260/245.2 T
4,262,010 4/1981 Christensen et al. ........ 260/245.2 T
4,289,696 9/1981 Smale .......................... 260/245.2 T

FOREIGN PATENT DOCUMENTS 78300522.6 6/1979 European Pat. Off. .
79301646.0 3/1980 European Pat. Off. .

Primary Examiner—Mary C. Lee
Attorney, Agent, or Firm—Frank M. Mahon; James A. Arno; Hesna J. Pfeiffer

[57] ABSTRACT

Disclosed is a process for the synthesis of carbapenem antibiotics I and their pharmaceutically acceptable salts and esters from 1:

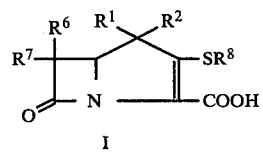 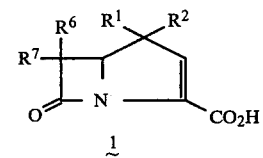

via sulfoxide 4

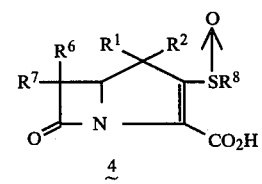

wherein: $R^7$, $R^6$, $R^1$, $R^2$ and $R^8$ are selected from hydrogen, alkyl, alkenyl, alkynyl, cycloalkyl, spirocycloalkyl, cycloalkylalkyl, alkylcycloalkyl, aryl, aralkyl, aralkenyl, aralkynyl, heteroalkyl, heteroaralkyl, heterocyclyl and heterocyclyalkyl.

9 Claims, No Drawings

PROCESS FOR THE PREPARATION OF CARBAPENEM ANTIBIOTICS

This invention relates to the synthesis of the antibiotic carbapenems of Structure I and their pharmaceutically acceptable salts and esters:

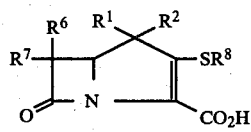

Antibiotics I are disclosed and claimed in co-pending, commonly assigned U.S. Patent Application Ser. No. 99,275 filed Dec. 3, 1979 of B. G. Christensen and D. H. Shih, now U.S. Pat. No. 4,312,871. To the extent that this copending application discloses I and its antibiotic utility, it is incorporated herein by reference.

Starting from 1, the synthesis proceeds via the reduction of sulfoxide 4.

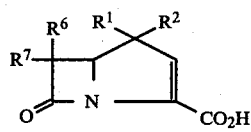

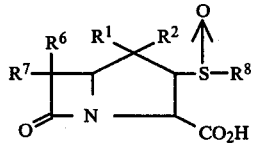

Starting materials 1, which are also antibiotics, are disclosed and claimed in co-pending, commonly assigned U.S. Patent Application Ser. No. 99,285 filed Dec. 3, 1979 of B. G. Christensen and D. H. Shih, now U.S. Pat. No. 4,262,009, to the extent that this application discloses 1, it is hereby incorporated by reference.

Relative to the foregoing structures I, 1, and 4, $R^1$, $R^2$, $R^6$, $R^7$ and $R^8$ are independently selected from the group consisting of hydrogen, substituted and unsubstituted: alkyl, alkenyl, and alkynyl, having from 1-10 carbon atoms; cycloalkyl, spirocycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the alkyl has 1-6 carbon atoms; heteroaryl, heteroaralkyl, heterocyclyl and heterocyclylalkyl; wherein the substituent or substituents relative to the above-named radicals are selected from the group consisting of: amino, mono-, di- and trialkylamino, hydroxyl, alkoxyl, mercapto, alkylthio, arylthio such as phenylthio, sulfamoyl, amidino, guanidino, nitro, chloro, bromo, fluoro, cyano, and carboxy; and wherein the hetero atom or atoms in the above-named heterocyclic moieties are selected from the group consisting of 1-4 oxygen, nitrogen or sulphur atoms; and wherein the alkyl moieties of the above-recited substituents have 1-6 carbon atoms.

DETAILED DESCRIPTION OF THE INVENTION

The process of the present invention may conveniently be summarized by the following reaction diagram:

DIAGRAM I

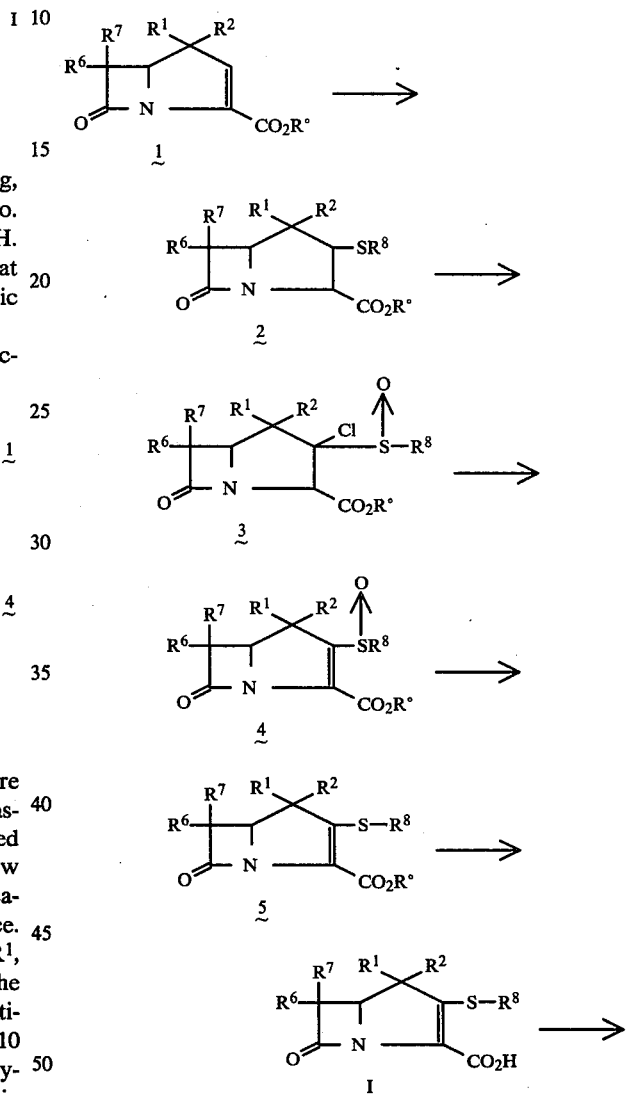

In words relative to diagram I, the reaction 1→2 is accomplished by treating 1 in a solvent such as dioxane, dimethylformamide, dimethylsulfoxide, acetonitrile, hexamethylphosphoramide, or the like in the presence of an approximately equivalent to excess of the mercaptan reagent $HSR^8$ wherein $R^8$ as defined above. A representative mercaptan reagent is $HSCH_2CH_2NHR^{8'}$ wherein $R^{8'}$ is hydrogen or a readily removable N-protecting group such as p-nitrobenzyloxycarbonyl, o-nitrobenzyloxycarbonyl, or the like in the presence of a base such as sodium hydrogen carbonate, potassium carbonate, triethylamine, diisopropylethylamine, or the like at a temperature of from −40 to 25° C. for from 1 to 72 hours. The mercaptan reagent, $HSCH_2CH_2NHR^{8'}$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours.

The oxidation of 2→3 is accomplished by treating 2 with iodobenzene dichloride in a solvent such as methylene chloride, chloroform, carbon tetrachloride or the like at a temperature of from 0° C. to 60° C. for from 10 min. to 2 hrs. Dehydrochlorination of 3 with a strong base such as 1,5-Diazabicyclo[5.4.0]undec-5-ene (DBU), or 1,5-Diazabicyclo[4.3.0]non-5-ene (DBN) or the like in a solvent such as ethyl acetate, acetone, THF, DMSO and DMF, at a temperature of from 0° C. to 60° C. for from 1 min. to 3 hrs. provides 4. Reduction of sulfoxide 4→5 is accomplished by treating 4 with a reducing agent such as 2-phenoxy-1,3,2-benzodioxaphosphone, 2-chloro-1,3,2-benzodioxaphosphone, triphenylphosphite, dichloroborane, iron pentacarbonyl, tin (II) chloride, diphosphorous tetraiodide, in a solvent such as CH₂Cl₂, chloroform, DMF, THF or the like at a temperature of from −20° C. to 40° C. for from 0.5 to 3 hours.

The final deblocking step 5→I is achieved by conventional procedure such as hydrolysis or hydrogenation. Typically 5 in a solvent such as dioxane-water-ethanol, tetrahydrofuran-aqueous dipotassium hydrogen phosphate-isopropanol or the like is treated under a hydrogen pressure of from 1 to 4 atmospheres in the presence of a hydrogenation catalyst such as palladium on charcoal, palladium hydroxide, or the like at a temperature of from 0° to 60° C. for from 0.5 to 4 hrs. to provide I.

Preparation of Starting Material 1

The starting material 1 is conveniently prepared by the following scheme:

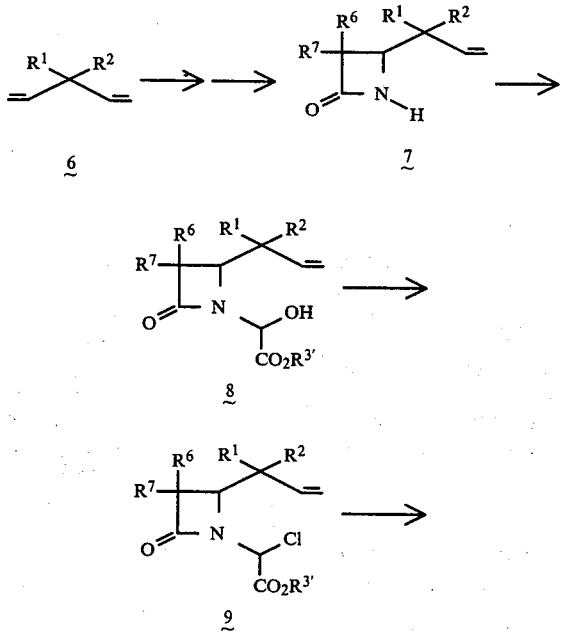

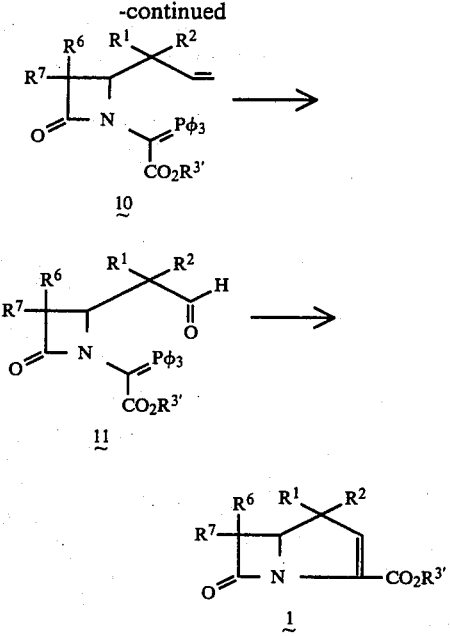

In words relative to the above diagram, the reaction 7→8 is accomplished by treating 7 in a solvent such as benzene, toluene, xylene, or the like at a temperature of from 80° to 130° C. for from 1 to 8 hours with a glyoxylate ester, HCOCO₂R³', wherein R³' is selected from the group consisting of convention protecting groups such as o-nitrobenzyl, p-nitrobenzyl, o-dinitrobenzyl, benzyl or the like. The halogenation reaction 8→9 may be conducted by any of a variety of well known halogenation means. Suitable reagents include SOCl₂, POCl₃, oxalyl chloride and the like. A preferred means of chlorination involves treating 8 in a solvent such as tetrahydrofuran (THF), ether, CH₂Cl₂, and the like with thionyl chloride in the presence of 1-2 equivalents (relative to the thionyl chloride) of base such as pyridine, triethylamine, quinoline and the like. Typically the reaction is conducted at a temperature of from −30° to 25° C. for from 0.5 to 1 hour. The resulting intermediate species 9 is isolated if desired by conventional procedures for later reaction, 4→5. Intermediate 10 is prepared from 9 by treating 9 in a solution such as dimethylformamide (DMF), dimethylsulfoxide (DMSO), THF, dimethoxyethane (DME) or the like with 1 to 1.5 equivalents of a phosphine such as triphenylphosphine, tributylphosphine, triethylphosphine, tris-(2-cyanoethyl)phosphine or the like. Typically the reaction is conducted under a nitrogen atmosphere at a temperature of 20° to 50° C., for from 0.5 to 2 hours. The reaction 10→11 may be achieved by any of a variety of well known oxidation reagents, such as RuO₄, OsO₄/NaIO₄, H₂O₂/Pb(OAc)₄, or O₃/Pφ₃. A particularly convenient means for the oxidating 10→11 is by treating 10 with ozone in a solvent such as methanol, trifluoroacetic acid or the like at a temperature of from −100° to 0° C., for from 0.1 to 4 hours, followed by treating the crude product with triphenyl phosphine at −18° C. to 0° C. for from 0.1 to 2 hours. The closure step 6→7 is conducted at a temperature of from about 0° to 100° C. for from 0.25 to 24 hours in a solvent such as benzene, toluene, dioxane, xylene, or DMF.

PREPARATION OF STARTING MATERIALS 6 AND 7

With respect to starting reagent 6, its preparation is generally described in *J. Amer. Chem. Soc.*, 74,661 (1952) by E. B. Reid and T. E. Gompf, *J. Org. Chem.*, 23,1063 (1958) by R. Ciola and K. L. Burwell, Jr., and Belgium Pat. No. 632,193 (1963) by R. Polster and E. Scharf. The following scheme summarizes the preparation of 6.

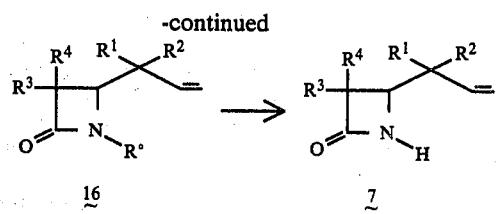

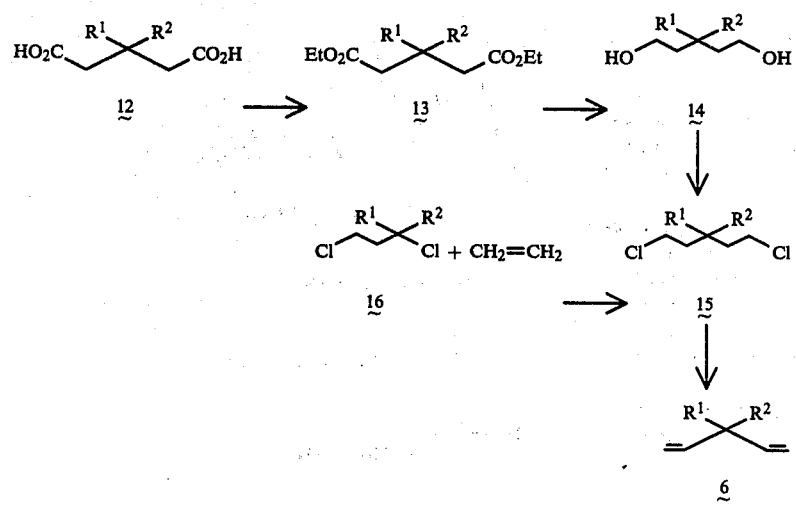

In words relative to the above scheme, the diester 13 is prepared by treating the diacid 12 with thionyl chloride at reflux for two hours followed by reacting with ethanol at 80° C. for 4 hours. Reduction of the diester 13 with lithium aluminum hydride in ether at reflux for 4 hours followed by hydrolysis with 10% NaOH gives diol 14 which on further reaction with thionyl chloride gives dichloride 15. The dichloride 15 can be alternatively prepared by treating 16 with ethylene in the presence of aluminum chloride. Treatment of the dichloride 15 with base such as 2-methylquinoline, DBU or sodium hydroxide in polyethylene glycol gives the expected 1,4-pentadiene 6.

Preparation of 7 is summarized in the following scheme:

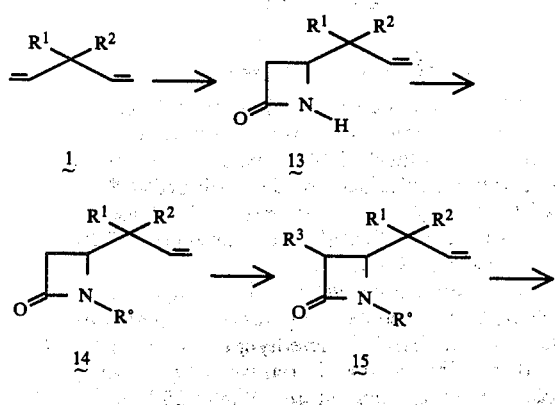

In words relative to the above scheme, the substituted azetidinone 7 is prepared by reacting a 1,4-pentadiene with chlorosulfonylisocyanate at 25° C. to 60° C. in a pressurebottle for 3–12 days, then the resulting mixture is hydrolyzed with aqueous sodium sulfite solution between pH 6.5–7.5 at 0° C. to 25° C. for from 5 minutes to 60 minutes.

Azetidinone 13 is transformed (13→14) to establish the protecting group R° which may be a triorganosilyl group, such as t-butyldimethylsilyl, t-butyldiphenylsilyl, triphenylsilyl, isopropyldimethylsilyl, for example, or may be 3,4-dimethoxybenzyl, for example. Silyl protection is preferred, and typically R° is established by treating 13 in a solvent such as dimethylformamide, acetonitrile, hexamethylphosphoramide, tetrahydrofuran or the like with a silylating agent such as t-butyldimethylchlorosilane, t-butyldiphenylchlorosilane, triphenylchlorosilane, or the like at a temperature of from −20° to 25° C. for from 0.5 to 24 hours in the presence of a base such as triethylamine, diisopropylamine or imidazole. Alkylation of 14 provides 15. Typically, 14 is treated with a strong base such as lithium diisopropylamide, sodium hydride, phenyl lithium or butyl lithium or the like in a solvent such as tetrahydrofuran (THF), ether, dimethoxyethane or the like at a temperature of from −80° C. to 0° C., whereupon the alkylating agent of choice, $R^3X$ is added ($R^3$ is as described above and X is chloro, bromo or iodo; alternatively the alkylating agent may be $R^3$-tosylate, $R^3$-mesylate or an aldehyde or ketone such as acetaldehyde and the like) to provide mono- alkylated species 15. When desired dialkylated species 16 may be obtained from 15 by repeating the alkylating procedure 14→15. Species 7 is obtained from 15 or 16 by acid hydrolysis.

In the generic description of the present invention (I, above), the substituents $R^1$, $R^2$, $R^6$, $R^7$ and $R^8$ are preferably selected from the group consisting of hydrogen;

substituted and unsubstituted: straight and branched loweralkyl having from 1 to 10 carbon atoms; cycloalkyl having from 3 to 6 carbon atoms; cycloalkylalkyl wherein the cycloalkyl moiety comprises 3 to 6 carbon atoms and the alkyl moiety comprises 1 to 10 carbon atoms; alkylcycloalkyl wherein the alkyl moiety comprises 1 to 6 carbon atoms and the cycloalkyl moiety comprises 3 to 6 carbon atoms; aryl such as phenyl and naphthyl; aralkyl such as benzyl, phenethyl and the like; heterocyclyl (saturated and unsaturated) comprising mono- and bicyclic structures having from 5 to 10 ring atoms wherein one or more of the hetero atoms is selected from oxygen, nitrogen or sulphur, such as thiophene, imidazolyl, tetrazolyl, furyl and the like; heterocyclylalkyl which comprises the immediately preceding heterocyclyl moieties and the alkyl moiety comprises from 1 to 10 carbon atoms; the substituent or substituents relative to the above-named radicals are selected from the group consisting of amino, hydroxyl, cyano, carboxyl, nitro, chloro, bromo, iodo, fluoro, lower alkoxy having from 1 to 6 carbon atoms, mercapto, perhaloloweralkyl such as trifluoromethyl, loweralkylthio, guanidino, amidino, sulfamoyl, and N-substituted: sulfamoyl, amidino and guanidino wherein the N-substituent is loweralkyl having from 1 to 6 carbon atoms or aryl having 6–10 carbon atoms.

In the foregoing description of the invention, suitable reagents HSR$^8$ (1→2) are representatively illustrated by the following list:

HSCH$_2$CH$_2$CH$_2$NHCO$_2$PNB,
PNBO$_2$CNHCH$_2$CH$_2$CH$_2$SX,

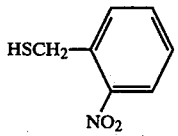

HSCH$_2$CH$_2$NHCO$_2$PNB
HSC(CH$_3$)$_2$CH$_2$NHCO$_2$PNB,
HSφ,
HSCH$_2$φ,
HSC(CH$_3$)$_3$,
HSCφ$_3$,

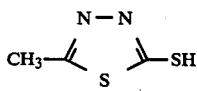

and the like (φ = phenyl; and PBN = p-nitrobenzyl),

CH$_3$SH,
CH$_3$CH$_2$SH,
CH$_3$(CH$_2$)$_2$SH,
(CH$_3$)$_2$CHSH,
CH$_3$(CH$_2$)$_3$SH,
(CH$_3$)$_2$CH(CH$_2$)$_2$SH,
CH$_2$≡CHCH$_2$SH,
CH≡CCH$_2$SH,

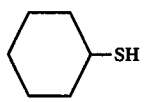

φ(CH$_2$)$_3$SH(φ = phenyl),
φ(CH$_2$)$_2$SH,
HO(CH$_2$)$_2$SH,
H$_2$N(CH$_2$)$_2$SH,
H$_2$N(CH$_2$)$_3$SH,
CH$_3$(CH$_2$)$_2$NH(CH$_2$)$_2$SH, -continued

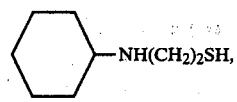

(CH$_3$)$_2$N(CH$_2$)$_2$SH,
(CH$_3$CH$_2$)$_2$N(CH$_2$)$_2$SH,
HO$_2$C(CH$_2$)$_2$SH,
φCH$_2$SH,

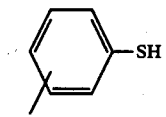

(n = 0, 1 or 2; X = Cl, Br, F, Cl, OCH$_3$, CH$_3$NH$_2$, $$\underset{\text{NHCCH}_3}{\overset{\text{O}}{\|}}).$$

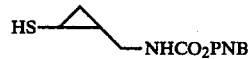

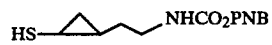

Similarly, suitable alkylating agents for establishing R$^6$ and/or R$^7$ at ultimate ring position 6 (17→18→2) are:

φCH$_2$CHO,
φCH$_2$CH$_2$CHO,
CH$_2$O,
CH$_3$I,
φCHBr,
CH$_3$COCH$_3$, $$\underset{\text{CH}_3\text{C}-\text{H}}{\overset{\text{O}}{\|}}.$$

EXAMPLE 1

Preparation of 3,3-Dimethyl-1,4-pentadiene

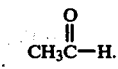    1

PROCEDURE A

β,β-Dimethylglutaric acid (obtained from Aldrich Chemical Company) (one mole), is refluxed for 2 hours with thionyl chloride (68% excess). After removal of excess thionyl chloride, absolute ethanol (109% excess) is added slowly. The mixture is refluxed for 3 hours then distilled to collect the product, diethyl β,β-dimethylglutarate (98% yield).

To a suspension of lithium aluminum hydride (24 g) in ether (860 ml) is added dropwise with rapid stirring a solution of diethyl β,β-dimethylglutarate (124 g in 250 ml ether). The mixture is refluxed for 6 hours, then cooled to room temperature. Water (25 ml) is added slowly. The mixture is then titrated with 10% NaOH until a clear organic layer is obtained. The organic layer is separated, dried over anhydrous sodium sulfate then evaporated in vacuo to give the resulting diol as an oil (90% yield), b.p. 95° at 1.0 mm. The 3,3-dimethyl-1,5-pentanediol (0.5 mole) is treated with thionyl chloride (1.05 mole) at reflux for 3 hours. After removal of excess thionyl chloride in vacuo, the 3,3-dimethyl-1,5-dichloropentane is obtained (90% yield).

3,3-Dimethyl-1.5-dichloropentane (41 g) is added dropwise at 170° C. to a mixture of 48 g of sodium hydroxide and 40 g of polyethylene glycol tetramer and the mixture is distilled to give 3,3-dimethyl-1,4-pentadiene (66%).

PROCEDURE B

At −40° C., 1,3-dichloro-3-methylbutane (50 g) is mixed with aluminum chloride (5 g). The ethylene is bubbled through the mixture for 4 hours. The mixture is allowed to warm to room temperature and hydrolyzed with water. The mixture is extracted with ethyl acetate to give 3,3-dimethyl-1,5-dichloropentane.

A mixture of 0.5 mole of 3,3-dimethyl-1,5-dichloropentane, 2-methylquinoline (2 moles), and sodium iodide (0.1 mole) is refluxed in a flask equipped with a Vigreaux column at the top of which is a condenser and take-off. The diolefin 1 is collected during 8 hrs reaction. The product is dried over anhydrous sodium sulfate.

EXAMPLE 2

Preparation of 3-methyl-1,4-pentadiene

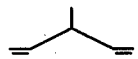
2

Following the procedure of Example 1(a), but replacing β,β-dimethylglutaric acid with an equivalent amount of β-methylglutaric acid, 3-methyl-1,4-pentadiene is obtained.

EXAMPLE 3

Preparation of 4-(1,1-dimethyl-pro-2-enyl)azetidin-2-one

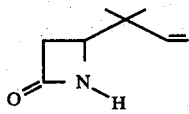
3

In a sealed tube, 3,3-dimethyl-1,4-pentadiene (9.6 g) and chlorosulfonyl isocyanate (14.2 g) are allowed to stand at room temperature for 6 days. The resulting mixture is diluted with methylene chloride and added slowly to a stirred aqueous solution which contains 20 g of Na₂SO₃ and 50 g of K₂HPO₄ at 0°–5° C. for 30 min. The organic layer is separated and dried over Mg₂SO₄. After evaporation, the crude product is chromatographed on silica gel GF eluting with EtOAc to give 3.

EXAMPLE 4

Preparation of 4-(1-methyl-pro-2-enyl)azetidin-2-one

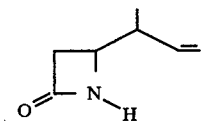
4

Following the procedure of Example 3, but replacing 3,3-dimethyl-1,4-pentadiene with 3-methyl-1,4-pentadiene, the title compound 4 is obtained.

EXAMPLE 5

Preparation of 5

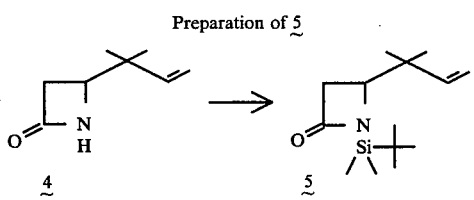

t-Butyldimethylchlorosilane (7.51 g) is added in one portion to an ice-cold, stirred solution of 4-(1,1-dimethyl-prop-2-enyl)-azetidin-2-one 4(6.54 g) and triethylamine (5.04 g) in anhydrous dimethylformamide (100 ml). The reaction mixture is stirred at 0°–5° C. for 1 hour and then allowed to warm to room temperature. Most of the solvent is removed under vacuum to give a residue which is partitioned between diethyl ether (250 ml) and water. The ethereal phase is washed with 2.5 N hydrochloric acid (50 ml), water (3×50 ml), and brine, dried with magnesium sulfate, filtered and evaporated under vacuum to provide an oil which is purified by chromatography on silica gel (20% ether in petroleum ether) to yield 5.

EXAMPLE 6

Preparation of 6

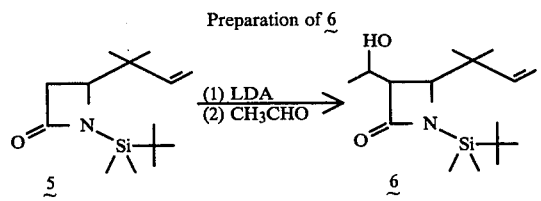

n-Butyllithium in hexane (26.25 mmol) is added slowly by syringe to a solution of diisopropylamine (26.25 mmol) in anhydrous tetrahydrofuran (100 ml) at −78° C. The resulting solution is stirred for 15 min. prior to the addition of a solution of 5 (25.0 mmol) in anhydrous tetrahydrofuran (25 ml). After stirring for 15 min. at −78° C., acetaldehyde (75 mmol) is added by syringe and the resulting solution is stirred at −78° C. for 5 min. Saturated aqueous ammonium chloride solution (15 ml) is added by syringe and the reaction mixture is allowed to warm to room temperature, then diluted with ether (250 ml) and washed with 2.5 N hydrochloric acid solution (2×50 ml), water (100 ml) and brine and dried over magnesium sulfate. Solvents are removed in vacuo and the residue is chromatographed on silica gel (1:1, ether: petroleum ether) to give the expected product 6.

EXAMPLE 7

Preparation of 7

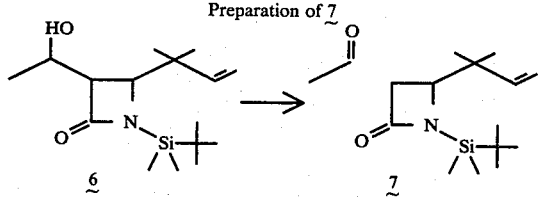

A. Trifluoroacetic anhydride (7.5 mmol) is added dropwise by syringe to a solution of dimethylsulfoxide (10 mmol) in anhydrous methylene chloride (15 ml) at −78° C. The resulting mixture is stirred at −78° C. for 20 min. A solution of 6 (5.0 mmol) in methylene chloride (15 ml) is added by syringe and the cooling bath is removed. After an additional 1 hr., the reaction mixture is diluted with methylene chloride (100 ml), washed with water (50 ml) and brine and dried over magnesium sulfate. Removal of solvents in vacuo yields crude products which is chromatographed on silica gel (2:1, petroleum ether:ether) to yield 7.

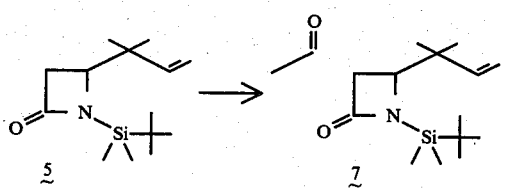

B. n-Butyllithium in hexane (4.10 mmol) is added by syringe to a solution of diisopropylamine (4.10 mmol) in anhydrous tetrahydrofuran (16 ml) at −78° C. The resulting solution is stirred at −78° C. for 15 min. prior to the addition of a solution of 1-(t-butyldimethylsilyl)-4-(1,1-dimethyl-prop-2-enyl)-azetidin-2-one 5 (2.0 mmol) in anhydrous tetrahydrofuran (2 ml). After an additional 15 min. at −78° C., the reaction mixture is added via a Teflon tube to a mixture of N-acetylimidazole (4.1 mmol) in anhydrous tetrahydrofuran (16 ml) at −78° C. The resulting yellow reaction mixture is stirred at −78° C. for 15 min., then quenched by addition of saturated aqueous ammonium chloride solution (10 ml). The reaction mixture is diluted with ether (100 ml) and washed with 2.5 N hydrochloric acid solution (25 ml) water (25 ml) and brine. The organic phase is dried over magnesium sulfate and concentrated in vacuo to yield crude products. This material is chromatographed on silica gel (2:1 petroleum ether:ether) to yield 7.

EXAMPLE 8

Preparation of 6

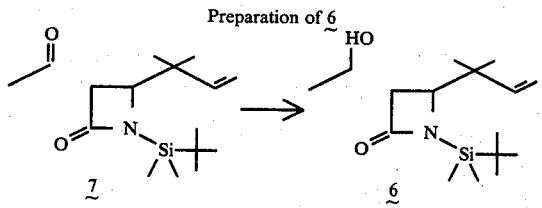

K-Selectride (potassium tri-(sec)-butylborohydride) in tetrahydrofuran (4.8 mmol) is added by syringe to a mixture of potassium iodide (2.0 mmol) and 7 (2.0 mmol) in anhydrous ether (20 ml) at room temperature.

The resulting mixture is stirred at room temperature for 2.5 hours, then quenched by addition of glacial acetic acid (9.6 mmol). The resulting mixture is diluted with ethylacetate (100 ml) and filtered through celite. Removal of solvents in vacuo gives crude products which is chromatographed on silica gel (1:1 ether:petroleum ether) to yield 1.90 g (95%) of 6.

EXAMPLE 9

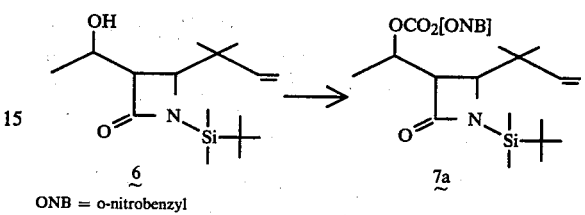

ONB = o-nitrobenzyl

Under anhydrous conditions at 0° C. a solution of 6 (3.50 g) in 60 ml methylene chloride is treated with 4-dimethylaminopyridine (3.32 g) and o-nitrobenzylchloroformate (5.88 g). The mixture is allowed to warm to room temperature and stirred for 1 hr. The resulting mixture is washed with 0.1 N, HCl, water, brine and water. The organic layer is separated, dried over Na$_2$SO$_4$ and allowed to evaporate in vacuo to give crude products. The crude products, dissolved in 20 ml ether and chilled at −5° C., give the o-nitrobenzyl alcohol (0.5 g) which is separated by filtration. Purification by HPLC (silica gel) eluting with 40% ethylacetate/cyclohexane to gives 7a.

EXAMPLE 10

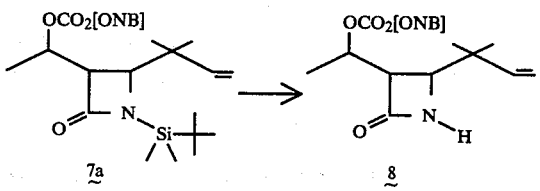

A solution of 7a (1.0 mol) in 20 ml of 9:1 (v/v) methanol-water is cooled to 0° C. Concentrated hydrochloric acid (0.34 ml) is added and the resulting solution is stirred at 0° C. for 15 min., then allowed to warm to room temperature. After 2.5 hrs, at room temperature the reaction mixture is diluted with ethyl acetate (25 ml), washed with water (10 ml) and brine, dried over magnesium sulfate and concentrated in vacuo to yield 8.

EXAMPLE 11

Preparation of 9

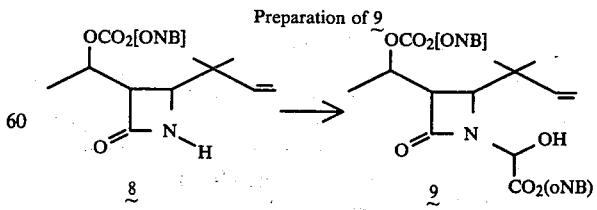

The azetidinone 8 (1.3 g) and o-nitrobenzyl glyoxylate hydrate (1.5 g) are refluxed in benzene (100 ml) for 6 hrs. The reaction apparatus is equipped with a Dean-Stark trap for removing water azeotropically. The solu-

EXAMPLE 12

Preparation of 11

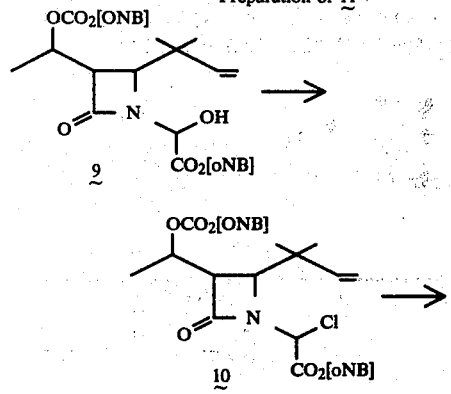

Under N₂, at −20° C., the carbinol 9 (0.82 g) in 5 ml THF is treated with thionyl chloride (204 mg) and pyridine (136 mg) for 10 min., then the mixture is allowed to warm to room temperature. The mixture is diluted with 10 ml benzene and filtered from solids. Evaporation of filtrate in vacuo gives the expected chloride which is then treated with triphenylphosphine (468 mg) in 5 ml DMF and stirred at room temperature for 1 hr. After evaporation of solvent in vacuo, the residue is dissolved in 70 ml CH₂Cl₂ and washed with 0.5 M sodium phosphate buffer (pH 6.9). The organic layer is separated, dried over MgSO₄ and chromatographed on silica gel eluting with 30% ethylacetate/CH₂Cl₂ to give 11.

EXAMPLE 13

Preparation of 13

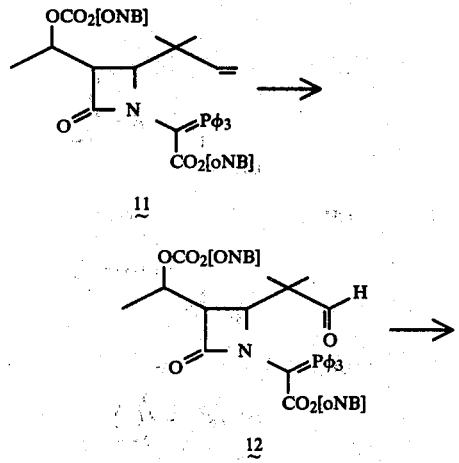

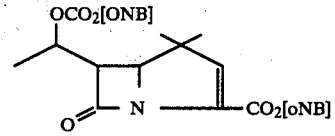

The ylide 11 (9.6 mg in 0.7 ml ethyl acetate) is mixed with trifluoroacetic acid (16 mg) and cooled to −78° C. Ozone is bubbled through the mixture until it is pale blue in color. Triphenylphosphine (3.7 mg) is added and nitrogen bubbled through the mixture for 10 minutes. The flask is transferred to an ice-bath and a saturated aqueous NaHCO₃ solution (1.0 ml) is added. After the mixture is stirred for 30 minutes, under N₂, the organic layer is separated, dried over MgSO₄. The solution is left to stand at room temperature overnight, then evaporated and chromatographed on silica gel eluting with 50% EtOAc/cyclohexane to give 13.

EXAMPLE 14

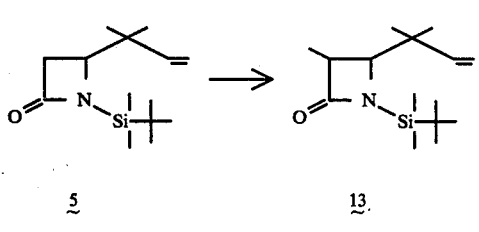

THF, 20 ml, is placed under N₂, treated with 1.54 ml diisopropylamine and cooled to −78° C. A solution of n-butyl lithium 1.97 M in hexane (5.6 ml) is added dropwise over 5 min. The reaction mixture is stirred at −78° C. for 10 min and then treated with 5 (2.14 g) in 15 ml THF which is added dropwise over 5 min. After another 10 min hexamethylphosphoramide (1.97 ml) is added. The mixture is stirred another 10 min, then treated with 2 ml of methyl iodide. The reaction mixture is stirred at −78° C. for 15 min and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C₆H₆ as eluant to give 13.

EXAMPLE 15

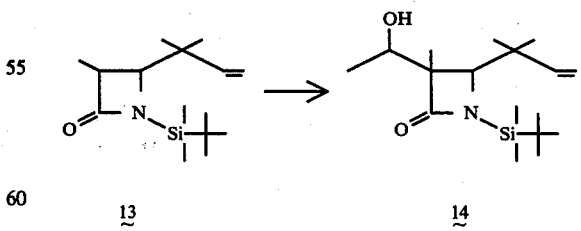

To a solution of 1.1 equivalents of freshly prepared lithium diisopropylamide in anhydrous tetrahydrofuran under a nitrogen atmosphere at −78° is added a solution of 13 in anhydrous tetrahydrofuran which has been cooled to −78° C. After two minutes, the resulting lithium enolate is treated with 3 equivalents of acetaldehyde. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethylacetate/benzene gives 14.

EXAMPLE 16

Following the procedure of the foregoing Examples, the following substituted azetidinones useful in the preparation of the compound of the present invention are obtained when the suggested substitution of reagents is made.

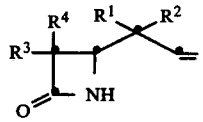

| Compound | $R^1$ | $R^2$ | $R^3$ | $R^4$ |
|---|---|---|---|---|
| (1.) | $CH_3$ | $CH_3$ | H | 2-$NO_2$-$C_6H_4$-$CH_2OC(O)OCH_2$- |
| (2.) | $CH_3$ | Et | H | $CH_3$ |
| (3.) | $CH_3$ | cyclopropyl | H | $C_6H_5C(O)$- |
| (4.) | $CH_3$ | $C_6H_5CH_2$ | H | $CH_3C(O)$- |
| (5.) | $CH_3$ | $CH(CH_3)_2$ | H | $C(CH_3)_2OH$ |
| (6.) | $CH_3$ | Ph | H | $CH(CH_3)N_3$ |
| (7.) | $CH_3$ | $CH_3CH_2CH_2$ | $CH_3$ | $CH(CH_3)OCO_2CH_2$-(2-$NO_2$-$C_6H_4$) |
| (8.) | Et | Et | $CH_3CH_2$ | $CH_2OCO_2CH_2$-(3-$NO_2$-$C_6H_4$) |
| (9.) | $CH_3$ | H | $CH_3$ | $CH_3C(O)$- |
| (10.) | Et | $CH_3$ | H | $CH(CH_3)OCO_2CH_2$-(2-$NO_2$-$C_6H_4$) |
| (11.) | Et | Et | $CH_3$ | $CH(CH_3)OCO_2CH_2$-(2-$NO_2$-$C_6H_4$) |
| (12.) | cyclopropyl | $CH_3$ | $CH_3$ | $CH_2OCO_2CH_2$-(2-$NO_2$-$C_6H_4$) |

EXAMPLE 16-continued

Following the procedure of the foregoing Examples, the following substituted azetidinones useful in the preparation of the compound of the present invention are obtained when the suggested substitution of reagents is made.

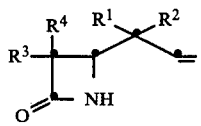

| Compound | R$^1$ | R$^2$ | R$^3$ | R$^4$ |
|---|---|---|---|---|
| (13.) | CH$_3$ | CH$_3$ | H | CH$_2$(CH$_2$—)CH$_2$OCO$_2$CH$_2$-(2-NO$_2$-C$_6$H$_4$) |
| (14.) | CH$_3$ | Et | H | iPr-OCH$_2$SCH$_3$ |
| (15.) | H | cyclopropyl | H | PhCH(CH$_3$)-OCO$_2$CO$_2$CH$_2$-(2-NO$_2$-C$_6$H$_4$) |
| (16.) | iPr (CH(CH$_3$)$_2$) | CH$_3$ | H | Ph— |
| (17.) | CH$_3$ | CH$_3$ | H | 4-pyridyl |
| (18.) | CH$_3$ | H | H | 4-pyridyl |
| (19.) | CH$_3$ | Et | H | CH$_3$CH-SCO$_2$CH$_2$-(2-NO$_2$-C$_6$H$_4$) |
| (20.) | R$^1$ + R$^2$ = SPIROCYCLOPROPYL | | H | iPr-OCO$_2$PNB |
| (21.) | CH$_2$CH$_2$Br | CH$_3$ | H | iPr-OCO$_2$PNB |

[PNB = p-nitrobenzyl]

EXAMPLE 17

Following the foregoing text and Examples, the following species (I) are obtained by analogy when the indicated substitution from Example 17 is made in Example 11 and the resulting product carried through the procedures of Examples 12–14.

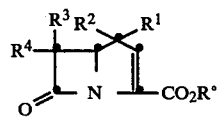

| Compound | R$^1$ | R$^2$ | R$^3$ | R$^4$ | R° |
|---|---|---|---|---|---|
| (1.) | CH$_3$ | —CH$_3$ | H | HOCH$_2$ | Na$^+$ |
| (2.) | Et | —CH$_3$ | H | —CH$_3$ | Na$^+$ |

-continued

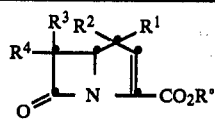

| Compound | R¹ | R² | R³ | R⁴ | R° |
|---|---|---|---|---|---|
| (3.) | CH₂CH₂CH₂ | —CH₃ | H | PhC(O)— (benzoyl) | H |
| (4.) | cyclopropyl | H | H | CH₃C(O)— | K⁺ |
| (5.) | cyclopropyl | —CH₃ | H | (CH₃)₂C(OH)— | Na⁺ |
| (6.) | PhCH₂ | CH₃ | H | CH₃CH(N₃)— | Na⁺ |
| (7.) | Ph | CH₃ | —CH₃ | CH₃CH(OH)— | —CH₂OC(O)CMe₃ |
| (8.) | CH₃ | CH₃ | CH₃CH₂— | HOCH₂— | H |
| (9.) | (CH₃)₂CH— | CH₃ | CH₃ | CH₃C(O)— | Na⁺ |
| (10.) | C₄H₉ | CH₃CH₂ | H | CH₃CH(OH)— | —CH₂—C₆H₄— |
| (11.) | Et | CH₃CH₂ | CH₃ | CH₃CH(OH)— | H |
| (12.) | CH₃ | cyclopropyl | CH₃ | HOCH₂— | Na⁺ |
| (13.) | cyclohexyl | CH₃ | H | CH₃CH(OH)CH₂— | (C₂H₅)₄N⁺ |
| (14.) | 2-(CH₂NH₂)C₆H₄ | CH₃ | H | CH₃CH(OCH₂SCH₃)— | H |
| (15.) | Ph | CH₃ | H | PhCH(OH)— | Na⁺ |
| (16.) | CH₃ | CH₃CH(CH₃)— | H | C₆H₅— | Na⁺ |
| (17.) | CH₃ | CH₃ | H | 4-pyridyl | Na⁺ |
| (18.) | Et | CH₃ | H | 2-pyridyl | Na⁺ |
| (19.) | CH₃ | CH₃ | H | CH₃CH(SH)— | K⁺ |
| (20.) | CH₂CH₂NH₂ | CH₃ | H | CH₃CH(OH)— | H |
| (21.) | CH₃ | CH₃ | H | CH₃CH(NH₂)— | H |

-continued

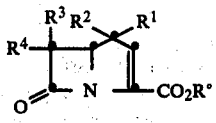

| Com- pound | R¹ | R² | R³ | R⁴ | R° |
|---|---|---|---|---|---|
| (22.) | R¹ + R² = spirocyclopropyl | | H | OH<br>\|<br>CH₃CH— | Na⊕ |

EXAMPLE 18

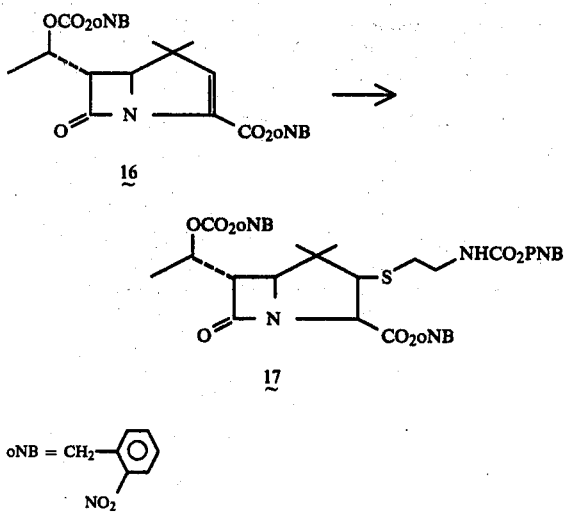

oNB = CH₂—⟨benzene with NO₂⟩

The 4,4-dimethyl descysteaminylthienamycin ester 16 (372 mg) is dissolved in DMF (2 ml). To the solution is added N-p-nitrobenzyloxycarbonylaminoisopropanethiol (200 mg) and potassium carbonate (97 mg). The mixture is stirred at room temperature for 3 hrs., then is diluted with ethyl acetate, washed with water. The organic layer is separated, dried over MgSO₄ and concentrated in vacuo to give 17 (a mixture of isomers).

EXAMPLE 19

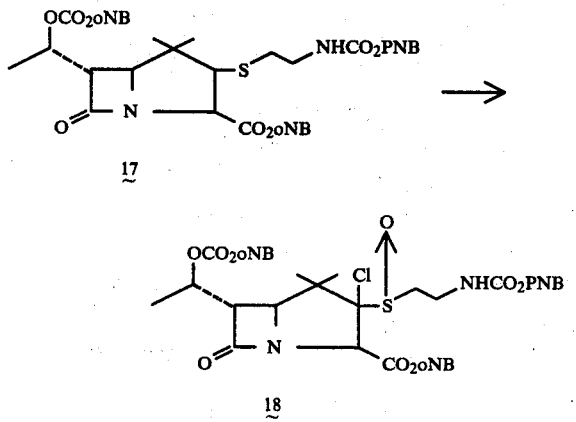

The azetidinone 17 (200 mg) is treated with iodobenzenedichloride (143 mg) in methylene chloride (10 ml) in the presence of pyridine (62 μl) and water (55 μl) at 0° C. for 1 hr. The mixture is evaporated in vacuo and the residue is chromatographed on silica gel plates eluting with ethyl acetate to give 18.

EXAMPLE 20

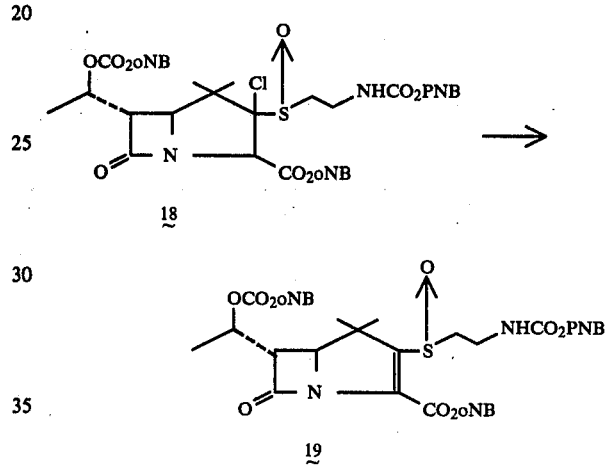

The chlorosulfoxide 18 (23 mg) in ethyl acetate (1.00 ml) is treated with 1.5-diazabicyclo [5.4.0]undec-5-ene (DBU) (4.2 μl) at room temperature for 2 hours. The mixture is evaporated in vacuo and the residue is chromatographed on silica gel plates eluting with 50% ethyl acetate/cyclohexane to give 19.

EXAMPLE 21

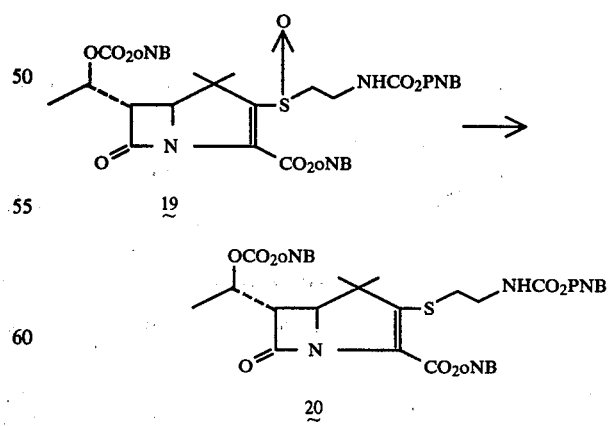

The sulfoxide ester 19 (5 mg) in carbon tetrachloride (0.15 ml) is treated with 2-phenoxy-1,3,2-benzodioxaphosphole (1.5 mg) and iodine (0.5 mg) at reflux for 1 hour. The resultant mixture is cooled, diluted with ethyl acetate and washed once with water, twice with 5% NaOH, then with aqueous hydrogen sulfite and water. The organic layer is dried with MgSO₄ and evaporated in vacuo to give 20.

EXAMPLE 22

Preparation of I:

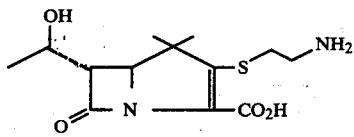

To 5.2 mg of 20 is added 0.60 ml dioxane, 0.05 ml ethanol, 0.35 ml deionized water and 0.01 ml of 1.0 M K₂HPO₄. To the resultant clear solution is added 5 mg of 10% Pd/C. The suspension is flushed with N₂, then closed under 50 psi H₂ atmosphere for 30–40 minutes. After centrifugation, the Pd/C is washed and centrifuged with 0.5 ml portions of deionized water. The combined centrifugates are extracted 5× with 2 ml portions ether. Residual ether is removed under vacuum and the aqueous solution is chromatographed on an XAD-2 column (20×140 mm) which is eluted with water to give the desired product I.

EXAMPLE 23

Following the foregoing text and Examples, the following species (I) are obtained by analogy when the indicated substitution of reagents is made.

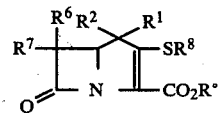

| Compound | R¹ | R² | R⁶ | R⁷ | R° | R⁸ |
|---|---|---|---|---|---|---|
| (1.) | CH₃ | —CH₃ | H | HOCH₂ | Na⁺ | —NH₂ |
| (2.) | Et | —CH₃ | H | —CH₃ | Na⁺ | NH₂ |
| (3.) | CH₃CH₂CH₂ | —CH₃ | H | PhC(=O) | H | ~~NHCH(=NH) |
| (4.) | cyclopropyl | H | H | CH₃C(=O) | K⁺ | —NHC(=NH)—NH₂ |
| (5.) | cyclopropyl | —CH₃ | H | (CH₃)₂C(OH)— | CH₂OCCCl₃(=O) | —CH₃ |
| (6.) | PhCH₂ | CH₃ | H | CH₃CH(N₃)— | H | >C(NH₂) |
| (7.) | Ph | CH₃ | —CH₃ | CH₃CH(OH)— | H | cyclopropyl-CH₂NH₂ |
| (8.) | CH₃ | CH₃ | CH₃CH₂— | HOCH₂— | —CH₂—Ph+ | —C₂H₅ \ |
| (9.) | (CH₃)₂CH | CH₃ | CH₃ | CH₃C(=O)— | H | —CF₂CH₂NH₂ |
| (10.) | C₄H₉ | —CH₂CH₂NH₂ | H | φCH₂CH(OH)— | H | —Ph |
| (11.) | Et | CH₃CH₂ | CH₃ | CH₃CH(OH)— | H | Ph—CH₂NH₂ |
| (12.) | CH₃ | cyclopropyl | CH₃ | HOCH₂— | Na⁺ | CH₃ |
| (13.) | cyclohexyl | CH₃ | H | CH₃CH(OH)CH₂— | (C₂H₅)₄N⁺ | CH₂NH₂ |

EXAMPLE 23-continued

Following the foregoing text and Examples, the following species (I) are obtained by analogy when the indicated substitution of reagents is made.

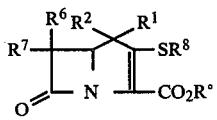

| Compound | $R^1$ | $R^2$ | $R^6$ | $R^7$ | $R°$ | $R^8$ |
|---|---|---|---|---|---|---|
| (14.) | Ph-CH₂NH₂ | CH₃ | H | CH₃CH(OCH₂SCH₃)— | H | —CH₂—cyclopropyl-CH₂NH₂ |
| (15.) | Ph | CH₃ | H | Ph-CH(OH)— | H | —CH₂CH₂C(=NH)—NH₃ |
| (16.) | CH₃ | CH₃CH(CH₃)— | H | Ph— | H | —CH₂CH(NH)CH₃ |
| (17.) | CH₃ | CH₃ | H | pyridyl | Na⁺ | —CH₂CH(NH₂)CO₂H |
| (18.) | Et | CH₃ | H | pyridyl | H | pyridyl |
| (19.) | CH₃ | CH₃ | H | CH₃CH(SH)— | K⁺ | —CH₃ |
| (20.) | $R^1 + R^2$ = spirocyclopropyl | | H | CH₃CH(OH)— | Na | —CH₂CH₂NHC(=NH)—H |

What is claimed is:

1. A process for preparing a compound having the structure:

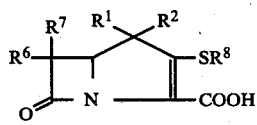

and the pharmaceutically acceptable salts thereof; wherein $R^1$, $R^2$, $R^6$, $R^7$ and $R^8$ are independently selected from the group consisting of hydrogen ($R^1$ and $R^2$ are not both hydrogen), substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; spirocycloalkyl having 3-6 carbon atoms; phenyl; aralkyl, aralkenyl, and aralkynyl wherein the aryl moiety is phenyl and the alkyl chain has 1-6 carbon atoms; thiophenyl, imidazolyl, tetrazolyl, furyl; thiophenylalkyl, imidazolylalkyl, tetrazolylalkyl and furylalkyl wherein the alkyl moiety contains from 1-10 carbon atoms, and wherein the substituent or substituents relative to the above-named radicals are selected from the group consisting of: amino, mono-, di-, and trialkylamino, hydroxyl, alkoxyl, mercapto, alkylthio, phenylthio, sulfamoyl, amidino, guanidino, nitro, chloro, bromo, fluoro, iodo, cyano and carboxy wherein the alkyl moieties of the above-recited substituents have 1-6 carbon atoms; comprising the steps of treating;

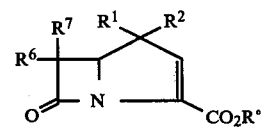

with $HSR^8$ to yield:

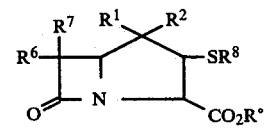

followed by treating with iodobenzenedichloride to yield:

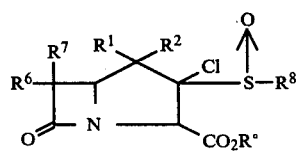

followed by dehydrochlorination in the presence of a strong base at 0° to 6° C., reduction with a reducing agent at −20° to 40° C. and deblocking by hydrogenation in the presence of a catalyst at 0° to 60° C. wherein R° is selected from the group consisting of hydrogen, an alkali metal, nitrobenzyl, tertiary butylbenzyl, trichloroacetoxymethyl, and triloweralkylkammonium.

2. A process for preparing a compound according to claim 1 wherein $R^1$ and $R^2$ are selected from hydrogen, alkyl, cycloalkyl, spirocycloalkyl, benzyl or phenyl; and $R^6$ is H or methyl and $R^7$ is alkyl, phenyl, aralkyl or hydroxyl-substituted alkyl, phenyl or aralkyl.

3. A process for preparing a compound according to claim 2 wherein $R^1$ and $R^2$ are selected from hydrogen, spirocyclopropyl, methyl, ethyl, isopropyl, t-butyl or phenyl and $R^7$ is 1-hydroxyethyl, methyl or hydroxymethyl.

4. A process according to claim 1 wherein $R^8$ is selected from the group consisting of:

H,
CH$_3$,
(CH$_2$)$_2$NH$_2$,
C(CH$_3$)$_2$CH$_2$NH$_2$, $$\text{C(CH}_3)_2\text{CH}_2\text{NH}-\overset{\overset{\displaystyle NH}{\|}}{C}-H,$$

$$\text{C(CH}_3)_2\text{CH}_2\text{NH}-\overset{\overset{\displaystyle NH}{\|}}{C}-CH_3,$$

,

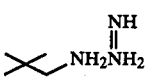—N(CH$_3$)$_2$

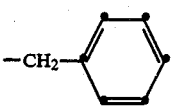—OCH$_3$

CH$_2$CH$_2$CH$_2$NH$_2$,
CH$_2$CH(CH$_3$)NH$_2$, $$\text{CH}_2\text{CH}_2\text{CH}_2\text{NH}-\overset{\overset{\displaystyle NH}{\|}}{C}-H,$$

$$\text{CH}_2\text{CH}_2\text{CH}_2\text{NH}-\overset{\overset{\displaystyle NH}{\|}}{C}-CH_3,$$

$$(\text{CH}_2)_2\text{NH}-\overset{\overset{\displaystyle NH}{\|}}{C}-H$$

$$(\text{CH}_2)_2\text{NH}-\overset{\overset{\displaystyle NH}{\|}}{C}-CH_3,$$

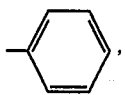

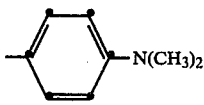

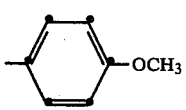

CH(CH$_3$)CH$_2$NH$_2$, $$\text{CH(CH}_3)\text{CH}_2\text{NH}-\overset{\overset{\displaystyle NH}{\|}}{C}-H$$

$$\text{CH(CH}_3)\text{CH}_2\text{NH}-\overset{\overset{\displaystyle NH}{\|}}{C}-CH_3$$

5. A process for preparing a compound according to claim 4 wherein $R^6$ is H or methyl; $R^7$ is selected from:

—CH$_2$OH $$\overset{\overset{\displaystyle OH}{|}}{CH_3CH}$$

$$\overset{\overset{\displaystyle NH_2}{|}}{CH_3CH}-$$

$$\overset{\overset{\displaystyle Cl}{|}}{CH_3CH}-$$

—CH$_2$—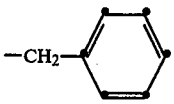

—CH(OH)—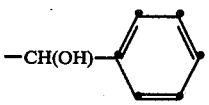

CH(OH)—CH$_2$—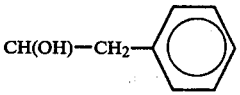

—CH$_3$
—CH$_2$CH$_2$

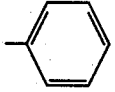

and $R^1$ and $R^2$ are selected from hydrogen, spirocyclopropyl; phenyl; cycloalkyl having 3–6 carbon atoms; alkyl having 1–6 carbon atoms; cyclopropylalkyl having 4–9 carbon atoms.

6. A process according to claim 5 wherein $R^1$ is hydrogen.

7. A process for preparing a compound according to claim 1 selected from the group consisting of:

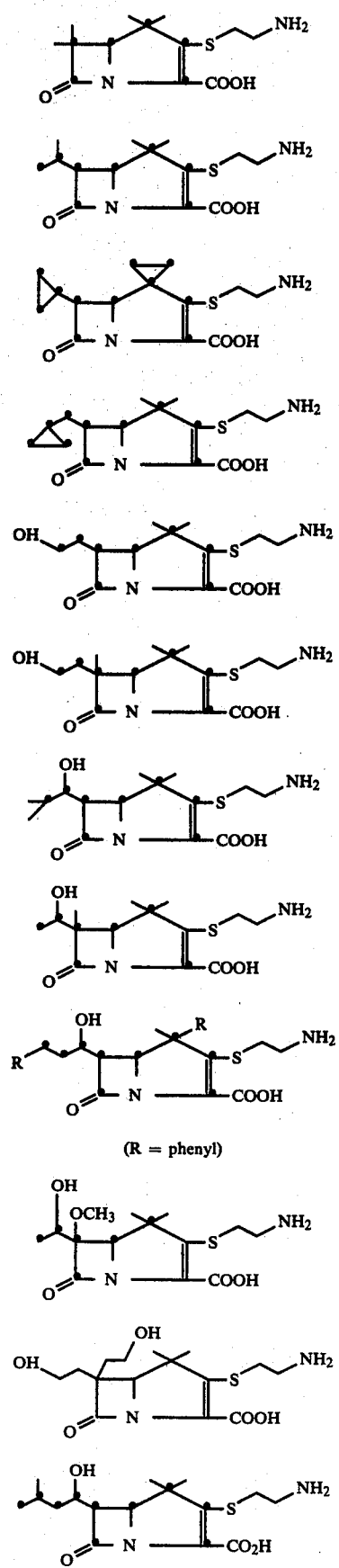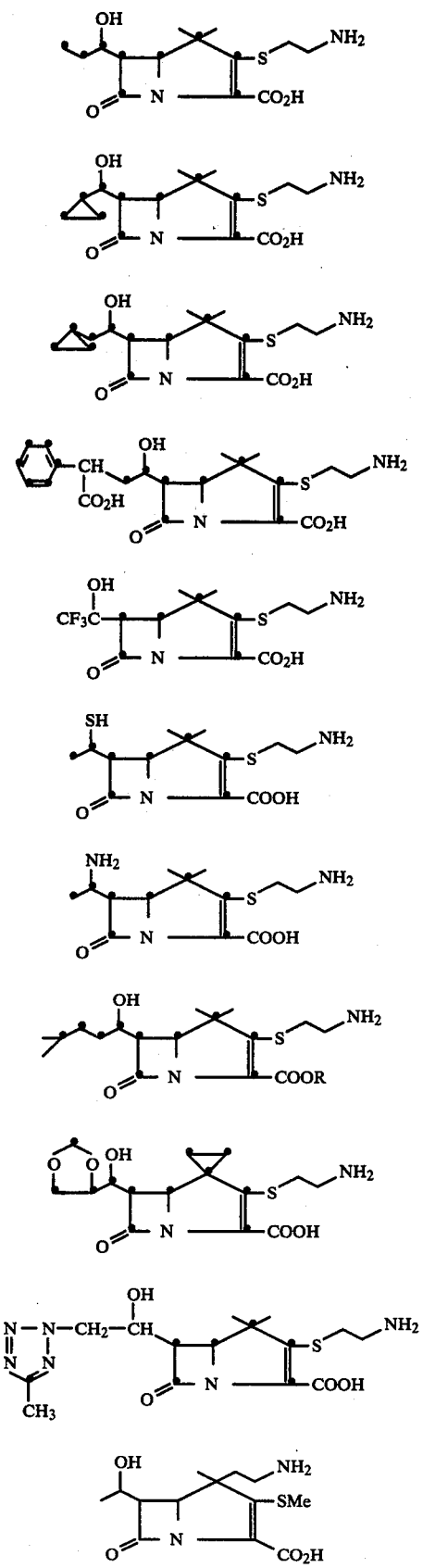

-continued
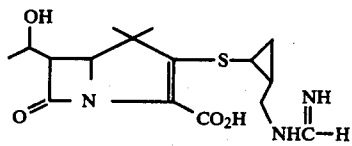
8. A process for preparing a compound according to claim 7 wherein the aminoethylthio side chain
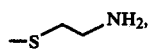
is replaced by a member of the group consisting of:
—SCF₃,
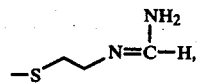
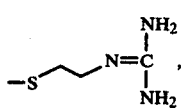
-continued
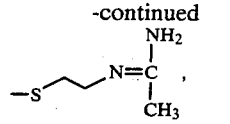
—S—(CH₂)ₙ—NH₂,
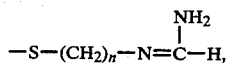
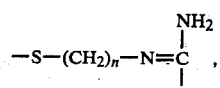
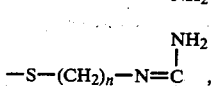
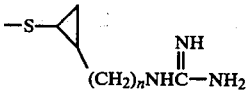
n = 1, 3, 4, 5 or 6.
9. A process for preparing a compound according to claim 1 wherein R¹ is hydrogen.
* * * * *